(12) United States Patent
Vanderveen et al.

(10) Patent No.: US 7,255,683 B2
(45) Date of Patent: Aug. 14, 2007

(54) SYSTEM FOR DETECTING THE STATUS OF A VENT ASSOCIATED WITH A FLUID SUPPLY UPSTREAM OF AN INFUSION PUMP

(75) Inventors: Timothy W. Vanderveen, Poway, CA (US); Robert D. Butterfield, Poway, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 540 days.

(21) Appl. No.: 10/749,367

(22) Filed: Dec. 31, 2003

(65) Prior Publication Data

US 2005/0145008 A1 Jul. 7, 2005

(51) Int. Cl.
*A61M 1/00* (2006.01)
(52) U.S. Cl. .......................... 604/118; 604/500; 417/53
(58) Field of Classification Search ................ 417/1, 417/4, 9, 53, 63; 73/1.57; 604/65, 67, 118, 604/120, 500
See application file for complete search history.

(56) References Cited

U.S. PATENT DOCUMENTS

| | | | |
|---|---|---|---|
| 4,394,862 A | 7/1983 | Shim | |
| 4,430,074 A | 2/1984 | Mooring | |
| 4,530,696 A | 7/1985 | Bisera et al. | |
| 4,533,347 A | 8/1985 | Deckert | |
| 4,553,958 A | 11/1985 | LeCocq | |
| 4,617,014 A | 10/1986 | Cannon et al. | |
| 4,650,464 A | 3/1987 | Ruiz et al. | |
| 4,673,389 A | 6/1987 | Archibald et al. | |
| 4,681,563 A | 7/1987 | Deckert et al. | |
| 4,696,671 A | 9/1987 | Epstein et al. | |
| 4,705,506 A | 11/1987 | Archibald | |
| 4,710,166 A | 12/1987 | Thompson et al. | |
| 4,714,463 A | 12/1987 | Archibald et al. | |
| 4,769,001 A | 9/1988 | Prince | |
| 4,816,019 A | 3/1989 | Kamen | |
| 4,828,545 A | 5/1989 | Epstein et al. | |
| 4,836,752 A | 6/1989 | Burkett | |
| 4,838,856 A | 6/1989 | Mulreany et al. | |
| 4,850,972 A | 7/1989 | Schulman et al. | |
| 4,865,584 A | 9/1989 | Epstein et al. | |
| 4,882,575 A | 11/1989 | Kawahara | |
| 4,898,576 A | 2/1990 | Philip | |
| 4,938,072 A | 7/1990 | Brown et al. | |
| 4,946,439 A | 8/1990 | Eggers | |
| 4,979,940 A | 12/1990 | Bobo, Jr. et al. | |
| 4,998,914 A | 3/1991 | Wiest et al. | |

(Continued)

*Primary Examiner*—Anthony D. Stashick
*Assistant Examiner*—Peter Bertheaud
(74) *Attorney, Agent, or Firm*—Fulwider Patton LLP (57) ABSTRACT

A system and method for determining whether the pressure in a fluid line upstream of an infusion pump is becoming lower as pumping draws fluid from the fluid line and fluid container due to a lack of proper venting. An initial pressure is sensed by an upstream pressure sensor at the start of an infusion. After a period of time, which may be determined either by monitoring infusion time or the number of pump cycles completed, a second pressure is sampled and compared to the initial pressure. Various analytical methods may be applied to the sensed pressures to determine upstream pressures or trends. Where an upstream pressure reading indicates a lack of proper venting, an alert signal is provided. Continuous monitoring may occur in which succeeding samples are compared to preceding samples to determine upstream pressures or trends.

20 Claims, 5 Drawing Sheets

U.S. PATENT DOCUMENTS

| | | |
|---|---|---|
| 5,087,245 A | 2/1992 | Doan |
| 5,088,981 A | 2/1992 | Howson et al. |
| 5,096,385 A | 3/1992 | Georgi et al. |
| 5,100,380 A | 3/1992 | Epstein et al. |
| 5,108,367 A | 4/1992 | Epstein et al. |
| 5,154,700 A | 10/1992 | Dansby |
| 5,211,201 A | 5/1993 | Kamen et al. |
| 5,304,126 A | 4/1994 | Epstein et al. |
| 5,312,334 A | 5/1994 | Hara et al. |
| 5,356,378 A | 10/1994 | Doan |
| 5,423,743 A | 6/1995 | Butterfield |
| 5,423,749 A | 6/1995 | Merte et al. |
| 5,464,392 A | 11/1995 | Epstein et al. |
| 5,554,115 A | 9/1996 | Thomas et al. |
| 5,803,917 A | 9/1998 | Butterfield et al. |
| 5,827,223 A * | 10/1998 | Butterfield .................... 604/65 |
| 5,935,106 A | 8/1999 | Olsen |
| RE36,871 E | 9/2000 | Epstein et al. |
| 6,213,972 B1 | 4/2001 | Butterfield et al. |
| 6,423,029 B1 | 7/2002 | Elsberry |
| 6,572,604 B1 * | 6/2003 | Platt et al. .................... 604/500 |
| 2001/0023345 A1 | 9/2001 | Wolff et al. |
| 2003/0069559 A1 | 4/2003 | Platt et al. |
| 2003/0130625 A1 | 7/2003 | Jacobson et al. |

\* cited by examiner

SYSTEM FOR DETECTING THE STATUS OF A VENT ASSOCIATED WITH A FLUID SUPPLY UPSTREAM OF AN INFUSION PUMP

BACKGROUND OF THE INVENTION

1. Field of the Invention

The present invention relates generally to a system and method for detecting when a negative-going pressure exists in an infusion line or container upstream of an infusion pump during administration of an infusion fluid to a patient. More specifically, the present invention relates to a system incorporating a container-side pressure sensor for sensing negative-going changes in the pressure within a fluid line, and for monitoring the container-side pressure to prevent negative-going pressure from developing due to an un-opened or blocked vent.

2. General Background and State of the Art

A common problem during infusion of therapeutic fluids into a patient occurs when the fluid to be infused is contained in burettes, bottles, or other non-flexible or partly flexible containers. When containers such as these are used as fluid reservoirs, they must be vented while the infusion is ongoing. If they are not vented, as fluid is drained from the bottle, burette, or other relatively rigid container, negative pressure is created within the container. This negative pressure may cause a reduction in flow, leading to inaccurate delivery of the therapeutic fluid.

Where an infusion pump is used to infuse the therapeutic fluid, the negative pressure building inside the container may also increase strain on the infusion pump, and may cause the pump to sound an alarm if the desired fluid infusion rate cannot be maintained. Another problem that can occur is that the negative pressure may result in air ingress into the system, especially at joints in the infusion line before the infusion line enters the infusion pump. This may result in air being entrained in the therapeutic fluid, and subsequently infused into the patient. While many infusion pumps use various types of air-in-line sensors to detect such entrained air and either halt the infusion or sound an alarm requiring attention by a care-giver before an amount of air that might injure the patient can be infused into the patient, prevention of such an occurrence is more cost-effective and efficient. Moreover, in cases where thin walled, yet rigid containers are used, the negative pressure may increase to such an extent that the thin walled containers collapse, possibly spilling their contents.

A vent is typically used in systems that will be infusing fluids from bottles, burettes, or other rigid or semi-rigid containers to prevent the build up of negative pressure as the fluid is drained from the container. However, if a care-giver forgets to open the vent or the particular drug or combination of drugs being infused wets the vent, the vent will not allow passage of air, resulting in a progressively increasing negative pressure in the container and fluid line as the pump attempts to draw fluid from the container.

What has been needed, and heretofore unavailable, is a system and method for determining when a container that requires venting to function properly is not being vented appropriately. Such a system would be able to detect the onset of negative pressure early enough so that a signal could be provided to care-givers before the infusion became inaccurate or damage was done to the pump. Moreover, such a system would be able to determine whether the intake or container-side pressure is not changing over time, indicating a stable infusion rate, or is decreasing as fluid is removed from the container, indicating lack of proper venting requiring attention by the care-giver. The present invention satisfies these and other needs.

INVENTION SUMMARY

Briefly and in general terms, the present invention is directed to a system and method for detecting when a container is not vented properly, leading to the formation of a reduced or negative-going pressure in a fluid line upstream of an infusion pump. It its broadest aspect, the present invention is embodied in an infusion pump that includes a sensor for detecting the pressure of fluid in the intake fluid line upstream of the infusion pump.

In another aspect, the present invention comprises an infusion pump system having a processor that monitors signals received from a sensor configured to monitor the pressure within the intake fluid line upstream of the infusion pump, and the processor also monitors a peristaltic pump within the infusion pump to track the status or position within its pumping cycle. In a further aspect, the processor samples the intake pressure multiple times each pumping cycle to compute a cycle-average, tracks the number of pumping cycles completed by the peristaltic pump, and processes the cycle-average pressures after a predetermined number of pump cycles have been completed. In a further aspect, the cycle-average pressure is sampled each time a selected number of pump cycles have been completed. After sampling the signals from the upstream pressure sensor, the processor determines whether there is a negative-going pressure present in the upstream infusion line.

In yet another aspect of the present invention, if the processor determines that a negative-going pressure is present in the upstream infusion line, the processor may direct that an alert be provided to care-givers notifying them that the infusion set-up requires attention. Such an alert may be visual, such as, for example, a message on a display, a blinking light, or a change in the color of text on a display. In another aspect, the alert may be auditory, such as an alarm. In still another aspect, the alert may take the form of a printed report. In still another detailed aspect, a combination of visual and auditory alerts may be provided. Where the infusion pump is in communication with other systems, such as an institution hospital administration system, patient monitoring system or the like, the alert may be recorded in a data base of alerts, and/or it may be associated and stored in a patient's medical administration record ("MAR").

In still another aspect of the present invention, the sensed intake pressure may be stored in a memory accessible by the processor. In yet a further aspect, the processor may wait a selected number of pump cycles, and, at the conclusion of the selected number of pump cycles, sample the cycle-average sensor signals and determine a second, later, cycle-average pressure value for the pressure in the upstream fluid line. The processor may then compare the second, later, cycle-average pressure value with the earlier pressure value to determine if there is a negative-going pressure in the fluid line. The processor may employ the slope of the cycle-average intake pressure signal versus time as well as its gauge value in determining whether a fault condition is present. The processor may then issue an alert indicating that attention to the infusion set-up is required.

In yet another aspect in accordance with the invention, a system for detecting the status of a vent associated with a fluid supply upstream of an infusion pump is provided, comprising an intake pressure sensor located upstream of an infusion pump, the intake pressure sensor configured to provide pressure signals representative of the pressure within the intake fluid line, and a processor configured to monitor a parameter representative of a status of the infusion pump such as the position of the mechanism within its pumping cycle and to sample the pressure signals received from the pressure sensor as a function of the status of the infusion pump, and, if the sampled signals indicate a negative-going pressure in the fluid line, to provide an alert. In yet another aspect, the negative-going cycle averaged pressure is indicative of a vent problem.

In still another aspect, the present invention includes a system wherein the infusion pump is a peristaltic pump and the monitored parameter is both the position within the peristaltic mechanism cycle and a value of the number of pump cycles the peristaltic pump has completed. In yet another aspect, the processor samples the signals or the cycle-average of the pressure signals received from the pressure sensor when the value of the monitored parameter exceeds a predetermined number of pump cycles.

In a further aspect, the processor periodically samples the cycle-average pressure signal received from the pressure sensor after a predetermined number of pump cycles has occurred. In one embodiment, the predetermined number of pump cycles is three.

In another aspect, the present invention includes a method of determining the status of a vent in a fluid line located upstream of a peristaltic infusion pump, the peristaltic infusion pump configured to pump fluid in a cyclical manner, the method comprising determining a value representative of the number of cycles that the have been completed by the infusion pump, sampling cycle-averaged pressure signals provided by a pressure sensor configured to sense the pressure in a fluid line upstream of the infusion pump, processing the cycle-averaged pressure signals to determine a value for the pressure in the upstream fluid line, and providing an alert if the rate of change of the cycle-averaged pressure exceeds a limit which may be a fixed value or a function of the size and type of container provided to the pump's control system via the control interface. In another aspect, the sampling of the cycle-average pressure occurs only when a predetermined number of pump cycles have been completed.

In a further aspect of the present invention, the method includes storing the value of the cycle-average pressures in a memory, sampling the cycle-averaged pressures after a predetermined number of cycles have been completed, determining a second cycle-averaged value for the pressure in the upstream fluid line, comparing the second value for the pressure to the first value for the pressure, and providing an alert signal if the second value is more negative than the first value by an amount either preset or a function of the container size and type provided to the pump's control system via the control interface.

In yet another aspect, the present invention is directed to a system for detecting a change in pressure in an infusion line upstream of an infusion pump, comprising a pressure sensor located upstream of an infusion pump adjacent an upstream infusion line, the pressure sensor configured to provide pressure signals representative of the pressure within the upstream fluid line, and a processor programmed to monitor a parameter representative of a status of an infusion of fluid into a patient, the processor also programmed to sample pressure signals received from the pressure sensor as a function of the status of the infusion, and to analyze the sampled signals to determine if the pressure in the upstream fluid line is decreasing.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
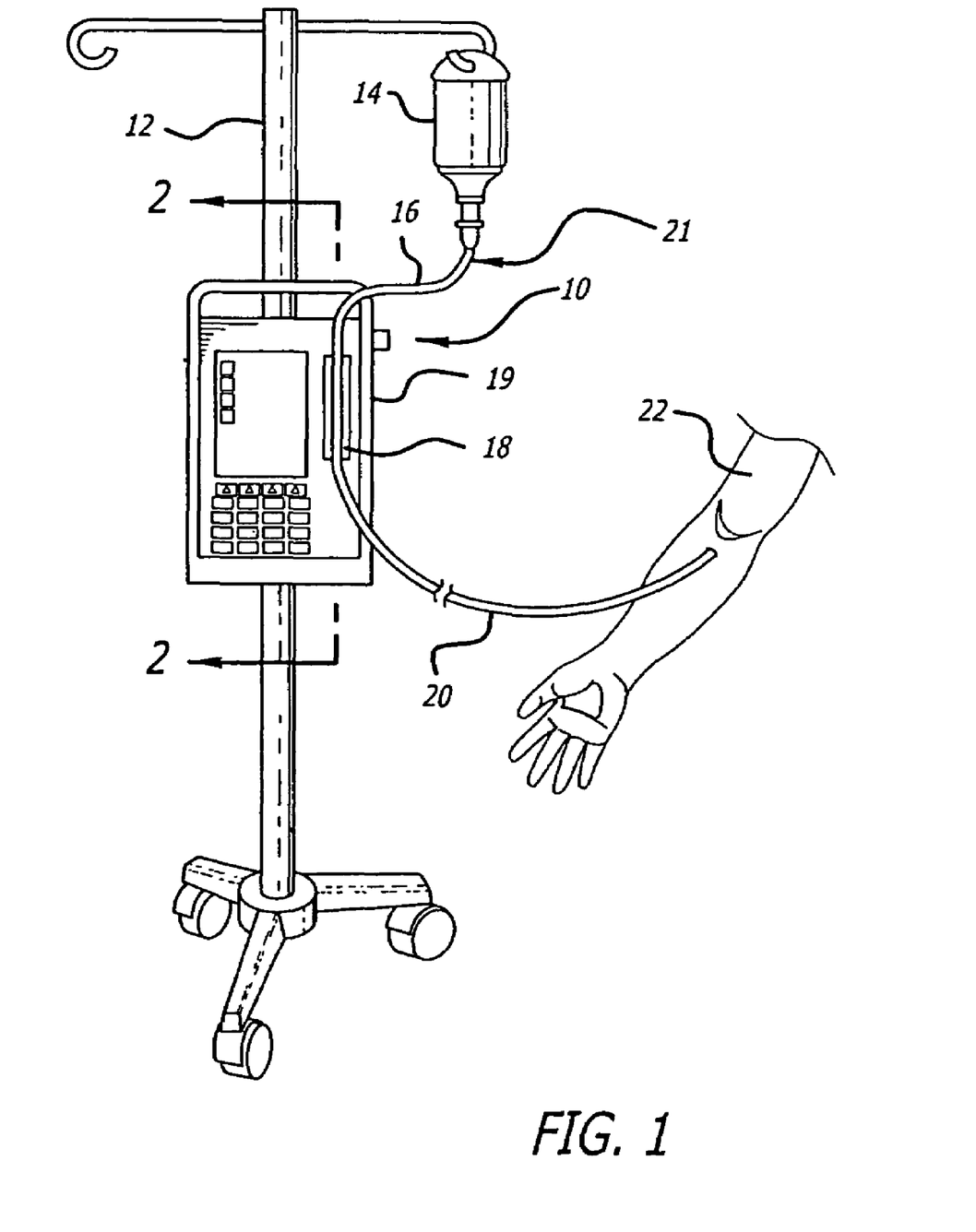
FIG. 1 depicts an infusing set-up including a fluid source and an infusion pump for infusing fluid from the fluid source into a patient.

Referring now to the drawings wherein like reference numerals among the drawing represent like or corresponding elements, there is shown in FIG. 1 an infusion pump set-up, generally designated by numeral 10, shown in use in its intended environment. In particular, the infusion pump set-up 10 is shown attached to an intravenous (I.V.) pole 12 on which a fluid source 14 containing an I.V. fluid is held. The fluid source 14 is connected in fluid communication with an upstream fluid line 16. The fluid line 16 is a conventional I.V. infusion-type tube typically used in a hospital or medical environment and is made of any type of flexible tubing appropriate for use to infuse therapeutic fluids into a patient, such as polyvinylchloride (PVC). A pumping tube segment 18 formed of flexible tubing is mounted in operative engagement with a peristaltic pump pumping apparatus 19, for pumping fluid through a downstream fluid line 20 into a patient's arm 22. It will be understood by those skilled in the art that the upstream fluid line 16, the flexible pumping portion 18, and the downstream fluid line 20 may be portions of a continuous length of flexible tubing, with the portions defined by the location of the peristaltic pump 19. For convenience, the entire length of tube shown in FIG. 1 is indicated by reference numeral 21. In this context, the term "upstream" refers to that portion of the flexible tubing 21 that extends between the fluid source 14 and the peristaltic pump 10, and the term "downstream" refers to that portion of the flexible tubing 21 that extends from the peristaltic pump 10 to the patient 22.

Figure 2:
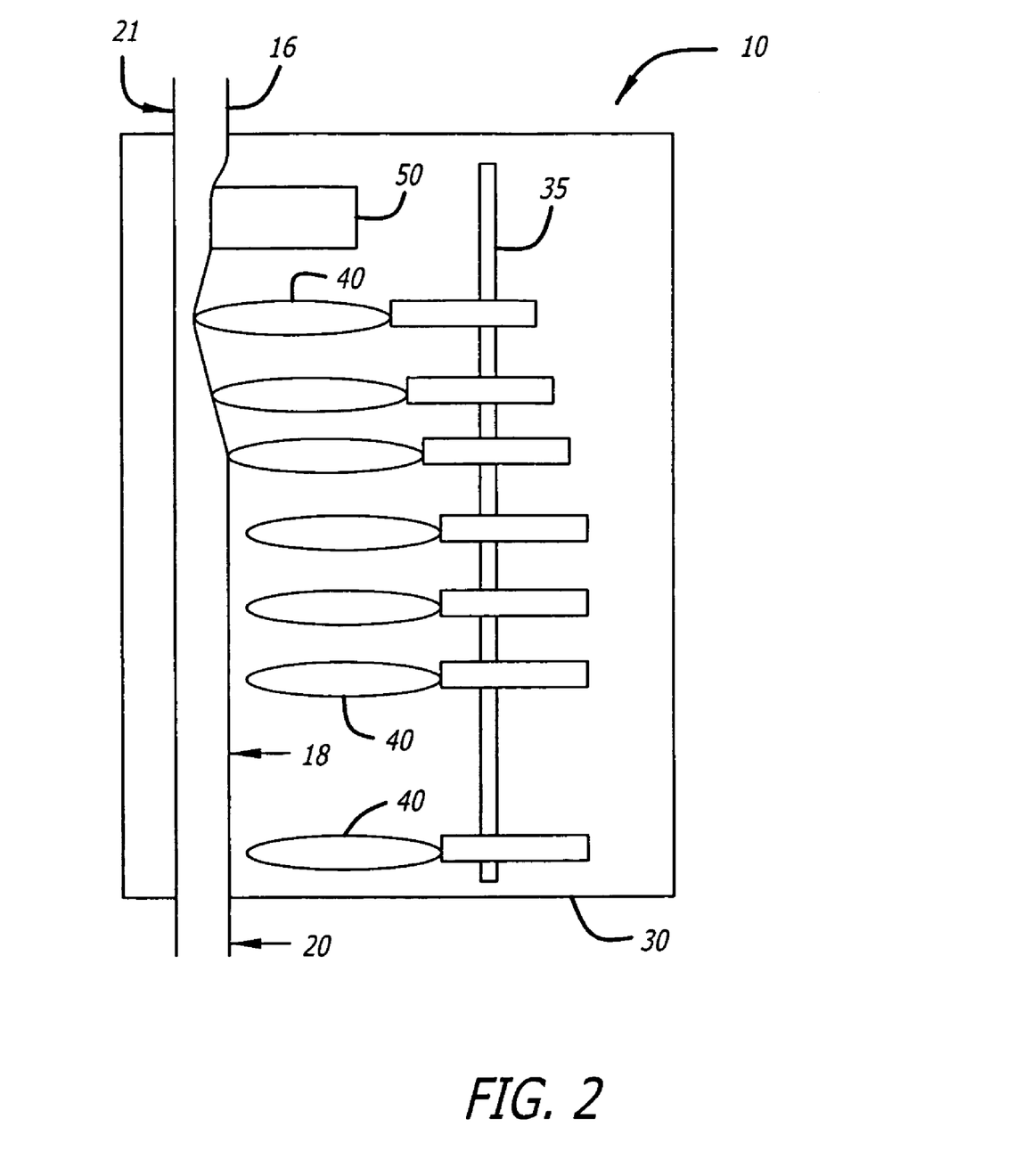
FIG. 2 is a side view of an exemplary peristaltic infusion pump including an upstream pressure sensor.

FIG. 2 depicts an enlarged view of the infusion pump 10 showing the interaction of the fluid line 21 with the elements of the peristaltic infusion pump. The fluid line 21 is disposed in the housing 30 of the pump 10 in such a manner that the flexible pumping portion 18 is in releasable contact with one or more pumping fingers 40 of the peristaltic infusion pump. Typically, such a peristaltic infusion pump utilizes a camshaft 35 with rotating cams, or other mechanism, to actuate one or more of the fingers 40 so that the fingers 40 sequentially press upon and squeeze the flexible portion 18 of the tube 21 to force fluid within the tube in a downstream direction. The operation of peristaltic mechanisms is well known to those skilled in the art and no further details are provided here.

An upstream intake pressure sensor or detector 50 is mounted in the housing 30 of the pump 10 to monitor the fluid pressure within the upstream, or container-side, tube 16. The upstream intake pressure sensor 50 may be any kind of detector known in the art that is capable of monitoring the fluid pressure within the tube 16 and providing signals that may be received by suitable electronics, such as, for example an amplifier, A/D converter, digital storage medium, such as a flash memory, or other type of suitable storage medium for storing values representative of the signals provided by the sensor. The digitized signals may also be provided to a computer or microprocessor for analysis, display, or reporting. Examples of pressure sensors or detectors suitable for monitoring the pressure within an upstream infusion line are capacitive, semiconductor, or resistive strain gauges, piezo-electric detectors, or other sensors or detectors known to those skilled in the art.

Those skilled in the art will also understand that the upstream intake pressure sensor and method embodied in the present invention are equally applicable to a rotary peristaltic or other cyclic infusion pump mechanisms, and such is intended to be within the scope of the present invention. Moreover, while the present invention is described in relation to an infusion pump having a processor or computer associated with the pump, it is intended that the invention also include systems wherein the microprocessor or computer is remote from, but in communication with the pump.

Figure 3:
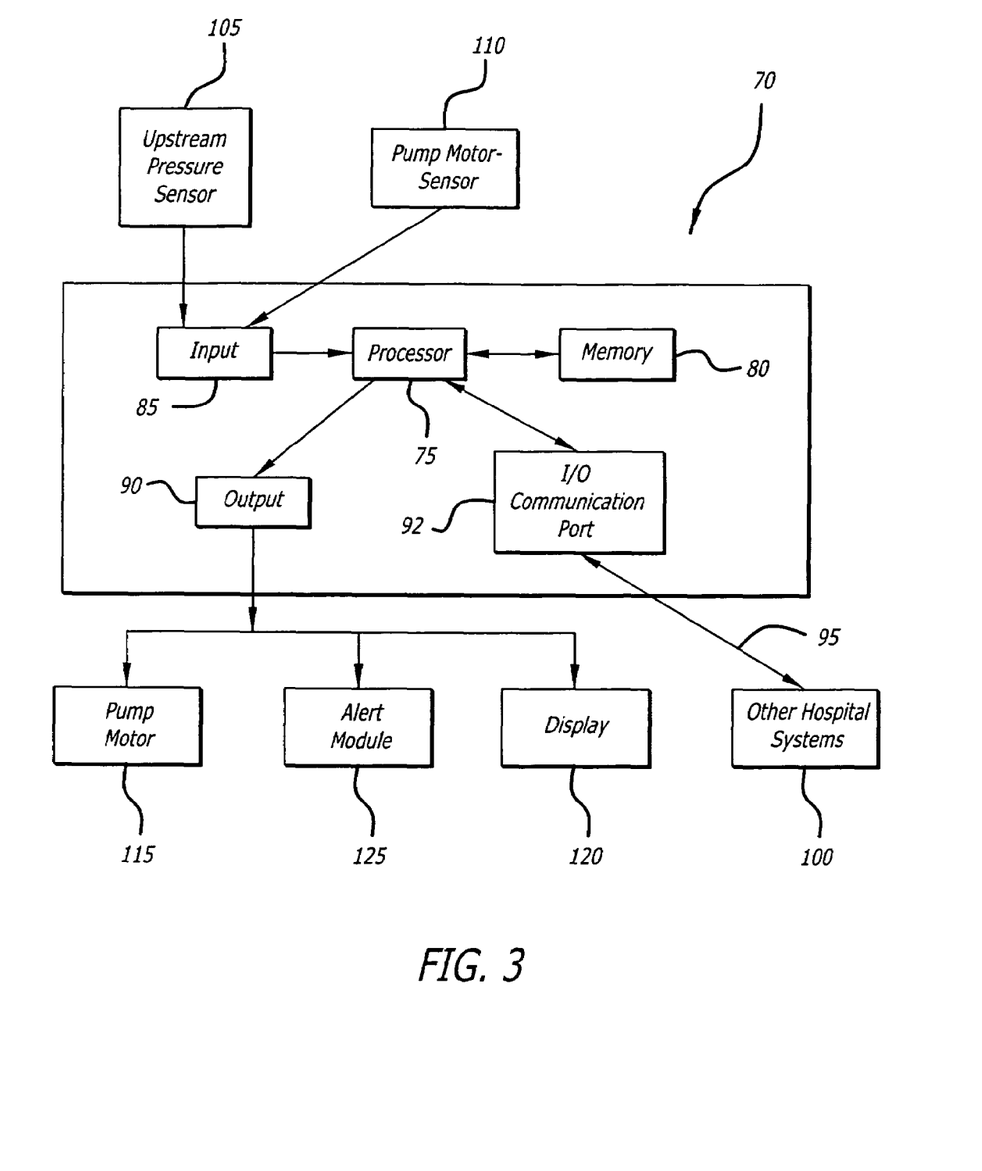
FIG. 3 is a schematic diagram of one embodiment of an infusion pump control system capable of being programmed to carry out the methods of the present invention.

Generally, as shown in FIG. 3, the infusion pump will include a control system 70 configured or programmed to control the operation of the peristaltic infusion pump so that a prescribed amount of medication or other therapeutic fluid is infused into the patient over a desired period of time. Such control systems typically include a microprocessor 75, a memory 80 associated with the microprocessor 75, one or more inputs 85 for inputting signals to the microprocessor, and one or more outputs 90 for outputting signals from the microprocessor.

The control system 70 may also be in communication with information systems, such as a pharmacy information system, hospital administration system, or other such systems in the institution using an input/output port 92 and communication means 95. The input/output port 92 may be any port configured to send and receive data using appropriate communication protocols, such as RS232 and the like. For example, the input/output port 92 may be a serial port, a parallel port, a USB, or other suitable port. It will also be understood that the input 85 and the output 90 may be combined in such a manner that all signals to and/or from the processor 75 are communicated through one or more input/output ports 92, rather than through separate inputs and outputs.

The communication means 95 may be a hard wired or wireless connection to another computer, a local area network, a wide area network, a telephone line to a remote server or client system, or the internet. The communication means may include specialized connection devices for connecting to optical fiber, coaxial cable, Ethernet cabling, or other communication lines. Alternatively, wireless connections may be used, which may also include the use of suitable transmitters and receivers as is known in the art. Such wireless connectivity may include use of infra red, RF, Bluetooth, or WiFi (IEEE 802.11b) communication means and the like. Additionally, the microprocessor 75 is commonly programmed using either embedded programming instructions or suitable software so that the microprocessor can carry out the tasks desired of it.

In one embodiment of the system and method of the present invention, the microprocessor 75 is capable of receiving signals from an upstream intake pressure sensor 105 through the input 85. The upstream intake pressure sensor 105 is disposed adjacent an upstream infusion line so as to monitor the fluid pressure within the upstream infusion line, and provide signals representative of the sensed pressure within the infusion line to the microprocessor 75. The microprocessor 75, as described above, is programmed using appropriate software or embedded commands to analyze the signals received from the upstream pressure sensor 50. After the analysis of the received upstream pressure signals is completed, the processor may output a signal through the output 90. This signal may be directed to the pump motor 115 to control the infusion of fluid to the patient.

The signal may also be directed to a display 120 to inform an operator of the status of the pump and/or the pressure within the upstream infusion line. This display may also include a means of providing a visual alert, such as a flashing display, blinking light, or a change in text color on the display to alert an operator that the infusion set-up requires attention.

The signal may also be directed to an alert module 125. This alert module may be a separate module of the processor that is controlling the pump, or it may be located at a location remote from the pump, and/or associated and in communication with a separate processor remote from the pump. The alert module 125 may be configured to provide visual, auditory, or a combination of visual and auditory notifications to care givers to alert the care giver that attention must be given to the infusion system. The alert module may produce signals that are communicated to consoles at the bed side, the nurse station, or a centrally located monitoring system. Additionally, various combinations of display changes and auditory alerts may be used to signify a priority of an alert, so that alerts which do not require immediate attention are less noticeable than alerts that require immediate attention to correct a problem before harm to the patient being infused can occur.

The alert module 125 may also provide signals representing the progress of the infusion, including any alerts generated due to a sensed reduced or negative pressure in the upstream infusion line, to a data base where the information is stored for later inspection and analysis. The data base may be associated with the pump, or the data base may be remote from the pump 10. For example, where the pump is controlled by a remote control system, the data base may be located and associated with the remote control system. In another embodiment, the data base may be part of an institutional information system which may be part of an enterprise wide network.

In another embodiment, the microprocessor 75 may also be configured to receive signals from a pump mechanism position sensor 110 through the input 85. In this embodiment, the processor 75 may monitor the function of the pump 10, collecting, analyzing, and storing information related to the infusion, such as, for example, the start time and completion time of the infusion, the amount of fluid infused, and the number of pump cycles that have been completed since the start of the infusion or since a selected time in the past and the intake pressure values at each of a plurality of corresponding pump mechanism positions. This information may be stored in the memory 80 for later retrieval and analysis, or the information may be communicated to another, remote, system using the communication means 95.

Figure 4:
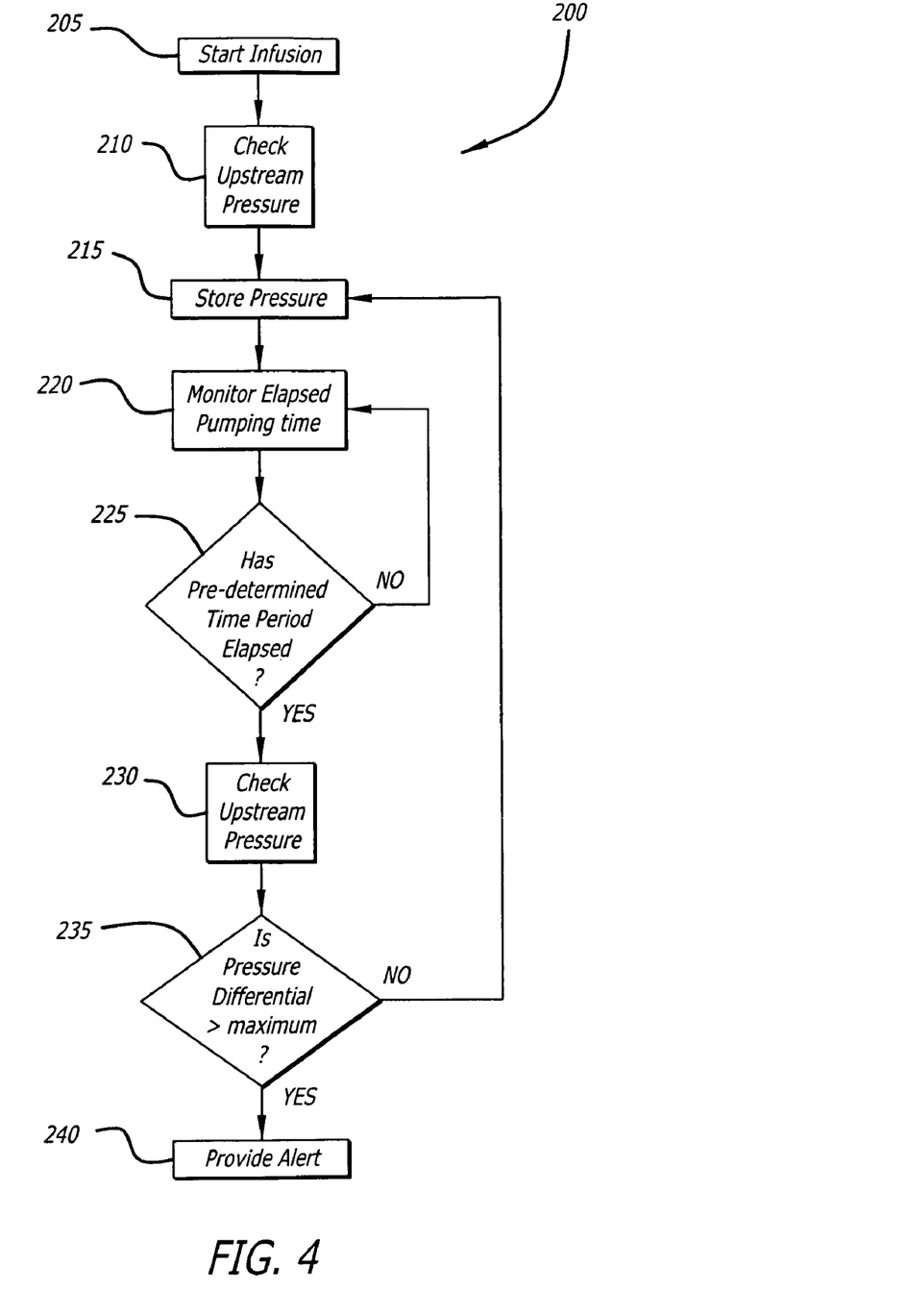
FIG. 4 is a block diagram of an embodiment of the methods of the present invention directed to detecting a reduced pressure in an upstream fluid line or container.

FIG. 4 is a schematic block diagram 200 illustrating one embodiment of the method of the present invention performed by the processor to determine the pressure in an upstream infusion line and to determine whether an alert should be given signifying that a negative pressure is building up in the upstream infusion line at a rate in excess of that expected under normal venting conditions. As discussed above, the processor is programmed to perform, among other processes, the steps set forth in FIG. 4. When the care-giver or operator starts the infusion by activating the infusion pump in box 205, the processor samples the signals representative of the pressure within the upstream infusion line provided by an upstream pressure sensor (FIG. 2) in box 210, converts the sampled signals into a pressure, and stores the pressure and the associated mechanism position (typically represented as an index, a step number or a rotational angle) in a memory associated with the processor (FIG. 3) in box 215.

The processor then computes the cycle-average pressure from the plurality of samples obtained from each individual cycle, monitors the elapsed pumping time in box 220 and waits for a selected period of time, which may be determined by the processor as being the time necessary for a selected number of processor clock cycles to occur, or some other measure of time determined from the operational characteristics of the processor, based on, for example, the clock speed of the processor as is well known in the art. After the pre-determined time period has elapsed or a specific movement of the mechanism detected, as determined in box 225, the processor may again sample the signals from the upstream pressure sensor in box 230, convert the sampled signals into a pressure value, convert these samples to a cycle-average pressure and compare the second cycle-average pressure value with the stored cycle-average pressure value in box 235 to determine if there has been an change in the pressure present in the upstream infusion line. If the predetermined period of time or movement has not elapsed or occurred, the processor continues to monitor the elapsed pumping time or motion, as depicted in box 220.

If the second cycle-averaged pressure value is less than the first cycle-averaged pressure value by more than a predetermined value or a value associated with the size and type of container as entered from the pump's user interface, the processor determines that an alert should be given to the care-giver, and provides that alert in box 240 by providing a visual or auditory alarm or notice that a fault condition exists and that the care-giver should inspect the infusion set-up and take appropriate corrective action, such as opening or unblocking a vent in upstream infusion line or container. If the comparison of the latter cycle-average pressure to the earlier cycle-average pressure does not indicate an excess reduction of pressure in the upstream infusion line, the processor returns to box 215 and stores the latest cycle-average pressure in the memory.

The processor may be programmed so that the process described above is carried out continuously throughout the infusion, providing a fail safe system to ensure proper venting of the upstream infusion line and fluid container. In such an embodiment, after the latest pressure value is stored in the memory in box 215, the processor continues to monitor the elapsed pumping time for an additional period, carrying out the remaining steps as set forth above for each pumping time interval.

When the latest cycle-average value of the upstream pressure is stored in the memory, the memory of the earlier value or values may simply be overwritten, or alternatively, the memory may be configured to store all of the pressure values determined during the infusion for later analysis. Multiple sequential cycle-average values may be used in conjunction with a digital weighting algorithm to compute an optimized slope of the cycle-average pressure signal which spans more than two cycles and thereby is more resistant to the effects of movement and other types of environmental artifact. Where all, or at least a portion, of the pressure values are stored, they are stored in a manner such that they are available to the processor in sequential order, so that the processor may compare the latest pressure value to the next earlier pressure value and/or perform more complex slope analysis as discussed above.

Figure 5:
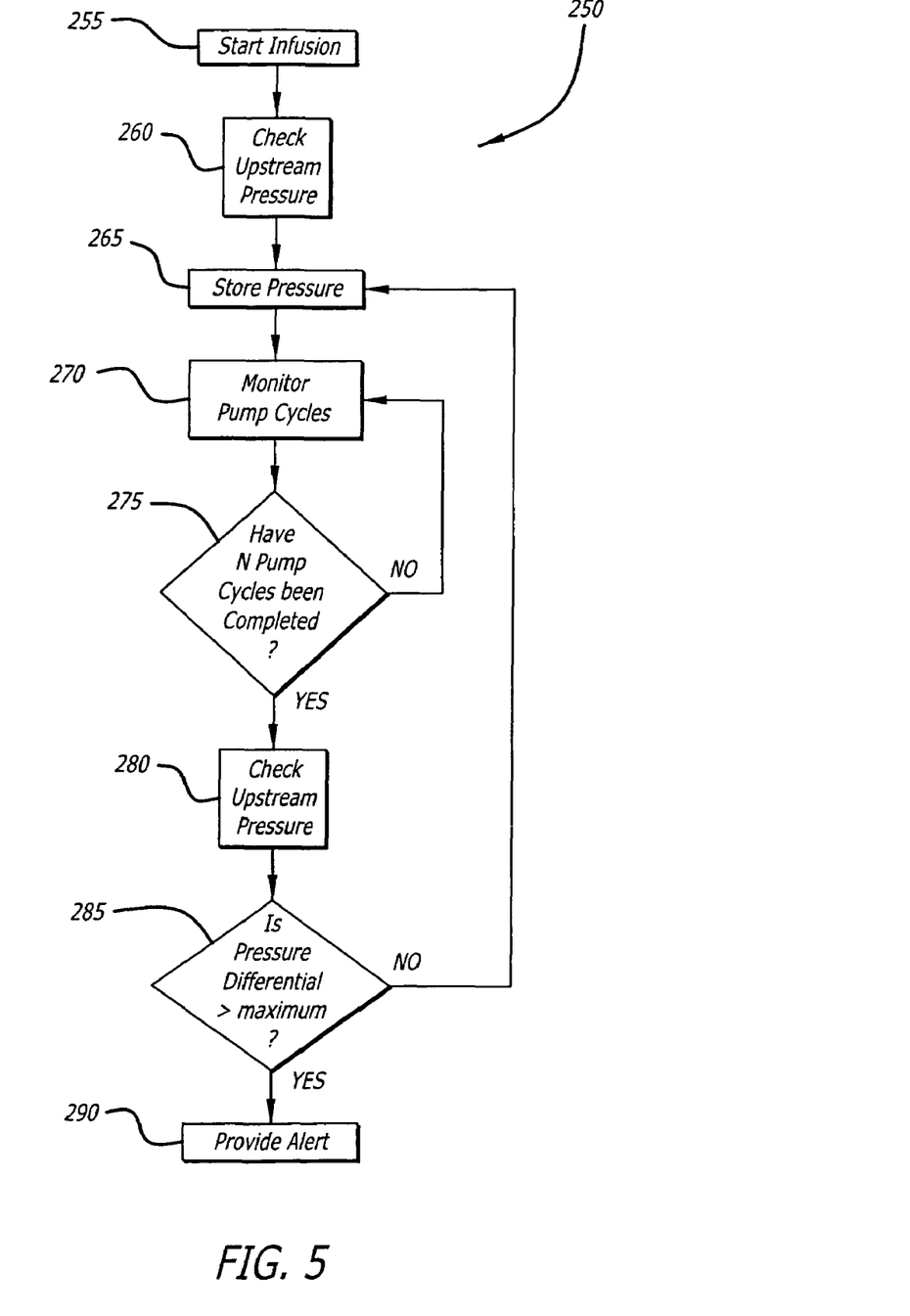
FIG. 5 is a block diagram of an alternative embodiment of the methods of the present invention directed to detecting a reduced pressure in an upstream fluid line or container.

In another embodiment of the present invention, as depicted in FIG. 5, the processor may determine the time frame for sampling the signals from the upstream pressure sensor by monitoring the number of pump cycles completed by the infusion pump. When the care-giver or operator starts the infusion by activating the infusion pump in box 255, the processor samples the signals representative of the pressure within the upstream infusion line provided by an upstream pressure sensor in box 260, converts the sampled signals into a pressure, averages multiple pressure samples associated with a mechanism cycle, and stores the cycle-average pressure in a memory associated with the processor in box 265.

The processor then monitors the number of pump cycles in box 270. If the pump has completed a selected number "N" cycles, as determined in box 275, then the program branches to box 280, and the signals from the upstream pressure sensor are again sampled, and the new cycle-average pressure value is compared to latest stored cycle-average pressure value in box 285 to determine the difference. If the selected number of cycles has not been completed, the program returns to box 270 and continues to monitor the number of pump cycles until the selected number of cycles is completed, then branching to box 280.

If the pressure sampled in box 280 is determined in box 285 to be less than the stored pressure value by more than an allowed maximum, the processor directs that an alert signal be provided in box 290. If the comparison in box 285 indicates that the latest sampled pressure is equal to or greater than the stored pressure, indicating that the pressure in the upstream line is stable or not reduced, then the program branches to box 265, stores the latest sampled pressure in the memory, and continues to monitor the number of pump cycles in box 270 until the next time that the upstream pressure should be sampled.

Alternatively, the processor may sample the cycle-averaged pressure difference values stored in the memory over a selected period of time and calculate, for example, an average value over the period of time to compare with the latest pressure value. One example of an analysis of this type is commonly called a moving average, which may be weighted or un-weighted, as those terms are understood in the art. In this manner, momentary changes in pressure, or errors in the signals provided by the upstream pressure sensor, may be filtered out to prevent unnecessary alarms. Other analysis methods, such as trend analysis or other methods may be utilized to ensure that alerts due to insignificant pressure changes or erroneous signals from the upstream pressure sensor are minimized while still providing protection from significantly reduced or negative pressure in the upstream infusion line.

While several particular forms of the invention have been illustrated and described, it will be apparent that various modifications can be made without departing from the spirit and scope of the invention.

We claim:

1. A system for detecting the status of a vent associated with a fluid container upstream of an infusion pump configured to draw fluid out of the fluid container through a fluid line by means of a pump mechanism in engagement with the fluid line, the vent having an open status at which the vent allows air to vent into the fluid container as fluid is drawn out of the fluid container resulting in pressure in the fluid line reducing at a rate expected under normal venting conditions, the vent having a blocked status at which venting of air into the container is blocked as fluid is drawn out of the fluid container resulting in pressure in the fluid line progressively reducing at a rate in excess of the rate expected under normal venting conditions, the system comprising:

a pressure sensor located upstream of the pump mechanism, the pressure sensor configured to provide pressure signals representative of the pressure within the fluid line upstream of the pump mechanism;

a processor in communication with the pressure sensor, the processor configured to sample the pressure signals received from the pressure sensor over a plurality of selected pump cycles, to compute for each of the plurality of selected pump cycles an average pressure value from the pressure signals received, to determine a progressive reduction in pressure in the fluid line based at least on the computed average pressure values, and to generate a blocked vent alert when the progressive reduction in pressure in the fluid line is determined to be at a rate in excess of the rate expected under normal venting conditions.

2. The system of claim 1 wherein the processor samples over a selected pump cycle when a predetermined number of pump cycles has occurred after a previously selected pump cycle.

3. The system of claim 1 wherein the processor periodically samples the signals received from the pressure sensor after a predetermined number of pump cycles have occurred.

4. The system of claim 3 wherein the predetermined number of pump cycles is three.

5. A method of determining the status of a vent in a fluid line located upstream of a peristaltic infusion pump, the infusion pump configured to draw fluid out of a fluid container in a cyclical manner, the vent having an open status at which the vent allows air to vent into the fluid container as fluid is drawn out of the fluid container resulting in pressure in the fluid line reducing at a rate expected under normal venting conditions, the vent having a blocked status at which venting of air into the container is blocked as fluid is drawn out of the fluid container resulting in pressure in the fluid line progressively reducing at a rate in excess of the rate expected under normal venting conditions, the method comprising:

sampling signals provided by a pressure sensor over a plurality of pump cycles, the pressure sensor configured to sense the pressure in the fluid line upstream of a pump mechanism of the infusion pump;

processing the sampled signals to determine an average value for the pressure in the upstream fluid line for each of the plurality of pump cycles;

determining a rate of change of the average values; and providing an alert when the rate of change exceeds a limit for normal venting conditions.

6. The method of claim 5 wherein sampling the signals provided by the sensor comprises sampling signals over a first selected pump cycle and sampling signals over a second selected pump cycle subsequent to completing a predetermined number of unselected pump cycles after the first selected pump cycle.

7. A system for detecting the status of a vent associated with a fluid container upstream of an infusion pump configured to draw fluid out of the fluid container through a fluid line by means of a pump mechanism in engagement with the fluid line, the vent having an open status at which the vent allows air to vent into the fluid container as fluid is drawn out of the fluid container resulting in pressure in the fluid line to reduce at a rate expected under normal venting conditions, the vent having a blocked status at which venting of air into the container is blocked as fluid is drawn out of the fluid container resulting in pressure in the fluid line to progressively reduce at a rate in excess of the rate expected under normal venting conditions, the system comprising:

a pressure sensor located upstream of the pump mechanism and adjacent the fluid line, the pressure sensor configured to provide pressure signals representative of the pressure within the fluid line upstream of the pump mechanism;

a data base located remotely from the infusion pump;

a memory disposed at the infusion pump; and a processor in communication with the pressure sensor, the data base, and the memory, the processor programmed to sample pressure signals received from the pressure sensor over a plurality of selected pump cycles comprising more than two pump cycles, to compute for each of the plurality of selected pump cycles an average value from the pressure signals received, to store the computed average values in the memory, to determine a rate of change of the stored average values, to generate a blocked vent alert when the determined rate of change exceeds a limit for normal venting conditions, and to provide the data base with information including any alert generated;

wherein the blocked vent alert includes a notification indicating that the vent should be opened.

8. The system of claim 1 further comprising a data base located remotely from the infusion pump, wherein the processor communicates with the data base to provide information regarding the progress of infusion to the data base, the information including any alerts generated.

9. The system of claim 1 wherein the processor is configured to compute a first average value from the pressure signals sampled over a first pump cycle, compute a second average value from the pressure signals sampled over a second pump cycle subsequent to the first pump cycle, determine whether the second average value is less than the first average value by more than a predetermined value, and provide the blocked vent alert when the second average value is determined to be less than the first average value by more than the predetermined value.

10. The system of claim 9 wherein the second pump cycle is a predetermined number of pump cycles subsequent to the first pump cycle.

11. The system of claim 9 wherein the fluid container has a size and type, and the predetermined value is associated with the size and type of the fluid container.

12. The system of claim 1 wherein the alert includes a notification indicating that the vent should be opened.

13. The system of claim 1 wherein the plurality of pump cycles comprises more than two pump cycles.

14. The system of claim 13 wherein the processor is configured to compute a slope from the average values computed from pressure signals received from the plurality of more than two pump cycles in determining the progressive reduction in pressure in the fluid line;

whereby determining the progressive reduction in pressure is resistant to effects of movement and environmental artifact.

15. The system of claim 14 wherein the processor is configured to use a weighting algorithm to compute the slope.

16. The method of claim 5 further comprising providing information to a data base including any alerts generated.

17. The method of claim 5 wherein providing the alert comprises providing a notification to open the vent.

18. The method of claim 5 wherein determining the rate of change of the average values comprises computing a slope from the average values;

whereby determining the rate of change of the average values is resistant to effects of movement and environmental artifact.

19. The method of claim 18 wherein computing a slope comprises using a weighting algorithm.

20. The method of claim 6 wherein:

processing the signals comprises processing the signals to determine a first average value for the pressure in the upstream fluid line for the first pump cycle and a second average value for the pressure in the upstream fluid line for the second pump cycle;

determining the rate of change of the average values comprises comparing the second average value to the first average value; and providing the alert when the rate of change exceeds the limit for normal venting conditions comprises providing the alert when the second average value is less than the first average value my more than a predetermined value.

* * * * *